United States Patent
Zhang et al.

(10) Patent No.: US 12,277,468 B2
(45) Date of Patent: Apr. 15, 2025

(54) MAGNETIC BEAD-BASED DETECTION METHOD, STORAGE MEDIUM, AND DETECTION DEVICE

(71) Applicant: BGI SHENZHEN, Guangdong (CN)

(72) Inventors: Wenwei Zhang, Guangdong (CN); Mei Li, Guangdong (CN); Weimao Wang, Guangdong (CN); Yuxiang Li, Guangdong (CN); Xun Xu, Guangdong (CN)

(73) Assignee: BGI SHENZHEN, Guangdong (CN)

( * ) Notice: Subject to any disclaimer, the term of this patent is extended or adjusted under 35 U.S.C. 154(b) by 0 days.

(21) Appl. No.: 18/651,099

(22) Filed: Apr. 30, 2024

(65) Prior Publication Data
US 2024/0281625 A1 Aug. 22, 2024

Related U.S. Application Data

(63) Continuation of application No. PCT/CN2021/127941, filed on Nov. 1, 2021.

(51) Int. Cl.
*G06K 7/08* (2006.01)
*G01N 33/543* (2006.01)
(Continued)

(52) U.S. Cl.
CPC ....... *G06K 7/087* (2013.01); *G01N 33/54326* (2013.01); *G06T 5/77* (2024.01);
(Continued)

(58) Field of Classification Search
CPC .. G06K 7/087; G06T 7/62; G06T 7/73; G06T 7/13; G06T 5/77; G06T 7/0002;
(Continued)

(56) References Cited

U.S. PATENT DOCUMENTS

2002/0164271 A1* 11/2002 Ho .................. G01N 33/588
436/164
2018/0214878 A1 8/2018 Chang et al.

FOREIGN PATENT DOCUMENTS

| CN | 109800631 A | 5/2019 |
| CN | 110187115 A | 8/2019 |
| CN | 110261602 A | 9/2019 |

OTHER PUBLICATIONS

International Search Report and Written Opinion mailed Jun. 29, 2022 in International Application No. PCT/ CN2021/127941, 12 pages.

* cited by examiner

Primary Examiner — Daniel A Hess
(74) Attorney, Agent, or Firm — Lee & Hayes, P.C.

(57) ABSTRACT

Provided are a magnetic bead-based detection method, a storage medium, and a detection device. The detection method includes: collecting a white light image of a to-be-detected solution, in which the to-be-detected solution is mixed with a to-be-detected sample and magnetic beads with a capture agent (S1); determining magnetic stripe regions in the white light image, and determining first magnetic bead regions based on the magnetic stripe regions (S2); selecting, by using a first neural network, second magnetic bead regions containing magnetic beads from the first magnetic bead regions, and obtaining a marker position of each of the magnetic beads (S3); and obtaining, by using a second neural network and based on each of the second magnetic bead regions, codes at code bits of a corresponding magnetic bead, and obtaining corresponding code information based on the codes of the code bits and the marker position of the magnetic bead (S4).

20 Claims, 8 Drawing Sheets

(51) Int. Cl.
 *G06T 5/77* (2024.01)
 *G06T 7/00* (2017.01)
 *G06T 7/13* (2017.01)
 *G06T 7/62* (2017.01)
 *G06T 7/73* (2017.01)

(52) U.S. Cl.
 CPC .............. *G06T 7/0002* (2013.01); *G06T 7/13* (2017.01); *G06T 7/62* (2017.01); *G06T 7/73* (2017.01); *G06T 2207/10024* (2013.01); *G06T 2207/10064* (2013.01); *G06T 2207/20081* (2013.01); *G06T 2207/20084* (2013.01); *G06T 2207/30204* (2013.01)

(58) Field of Classification Search
 CPC . G06T 2207/10024; G06T 2207/10064; G06T 2207/20081; G06T 2207/20084; G06T 2207/30204; G01N 33/54326
 USPC ........................................................ 235/449
 See application file for complete search history.

Code:011011101101  Code:111111111111

MAGNETIC BEAD-BASED DETECTION METHOD, STORAGE MEDIUM, AND DETECTION DEVICE

CROSS-REFERENCE TO RELATED APPLICATION

The present application is a continuation of International Application No. PCT/CN2021/1279419, filed on Nov. 1, 2021, which is hereby incorporated by reference in its entirety.

FIELD

The present disclosure relates to the technical field of biological detection, and more particularly, to a magnetic bead-based detection method, a storage medium, and a detection device.

BACKGROUND

In immunological assays and molecular diagnostic assays, multiple assays are an important means. The multiple assays refer to simultaneous measurement of a plurality of analytes in a single assay using a variety of capture agents. Each capture agent has specificity for different target macromolecules. In chip-based array multiple assays, each type of capture agent is affixed at a predetermined position on the chip. An amount of multiple targets in complex samples is determined by measuring signals of detection molecules at each position corresponding to a type of capture agent.

In suspension array multiple assays, magnetic beads are suspended in an assay solution. These magnetic beads contain recognition elements (e.g., "codes") that may be generated through embedding, or printing of one or more elements of the magnetic beads, or other manners. Each type of capture agent is fixed to magnetic beads having a same code. By collecting an image of the assay solution containing the magnetic beads and performing image recognition, signals transmitted by detection molecules on surfaces of the magnetic beads with predetermined codes are obtained. Moreover, the amount of the corresponding targets is reflected according to the signals. However, current algorithms for magnetic bead codes mainly adopt a traditional image processing algorithm, which is poor in robustness, is easily interfered by factors such as image quality, magnetic bead superposition, and impurities, and is slow in recognition speed.

SUMMARY

The present disclosure provides a magnetic bead-based detection method, a storage medium, and a detection device.

In a first aspect, the present disclosure provides a magnetic bead-based detection method. The detection method includes: collecting a white light image of a to-be-detected solution, where a to-be-detected sample and magnetic beads with a capture agent are mixed in the to-be-detected solution; determining magnetic stripe regions in the white light image; determining first magnetic bead regions based on the magnetic stripe regions; selecting, by using a first neural network, second magnetic bead regions containing magnetic beads from the first magnetic bead regions, and obtaining a marker position of each of the magnetic beads; obtaining, by using a second neural network and based on each of the second magnetic bead regions, codes at code bits of a corresponding magnetic bead; and obtaining corresponding code information based on the codes of the code bits and the marker position of the magnetic bead.

In a second aspect, the present disclosure provides a computer-readable storage medium, storing a computer program. The computer program, when executed by a processor, implements the magnetic bead-based detection method as described above.

In a third aspect, the present disclosure provides a detection device. The detection device includes a memory, a processor, and a computer program stored on the memory. The computer program, when executed by the processor, implements the magnetic bead-based detection method as described above.

For the magnetic bead-based detection method according to the embodiments of the present disclosure, a neural network is used for realizing azimuth determination and code recognition of the magnetic beads, resulting in the advantages of high robustness and fast operation speed. In addition, by reading fluorescence of a fixed region as magnetic bead fluorescence, the detection method has the advantages of fast speed, less susceptible to boundary ambiguity, high accuracy, and the like.

Additional aspects and advantages of the present disclosure will be provided at least in part in the following description, or will become apparent at least in part from the following description, or can be learned from practicing of the present disclosure.

BRIEF DESCRIPTION OF THE DRAWINGS

The above and/or additional aspects and advantages of the present disclosure will become apparent and readily understood from the following description of embodiments in conjunction with the accompanying drawings, in which.

DETAILED DESCRIPTION

Embodiments of the present disclosure will be described in detail below. The embodiments described with reference to the drawings are exemplary. The embodiments of the present disclosure will be described in detail below.

A magnetic bead-based detection method, a storage medium, and a detection device according to the embodiments of the present disclosure will be described below with reference to the drawings.

Figure 1:
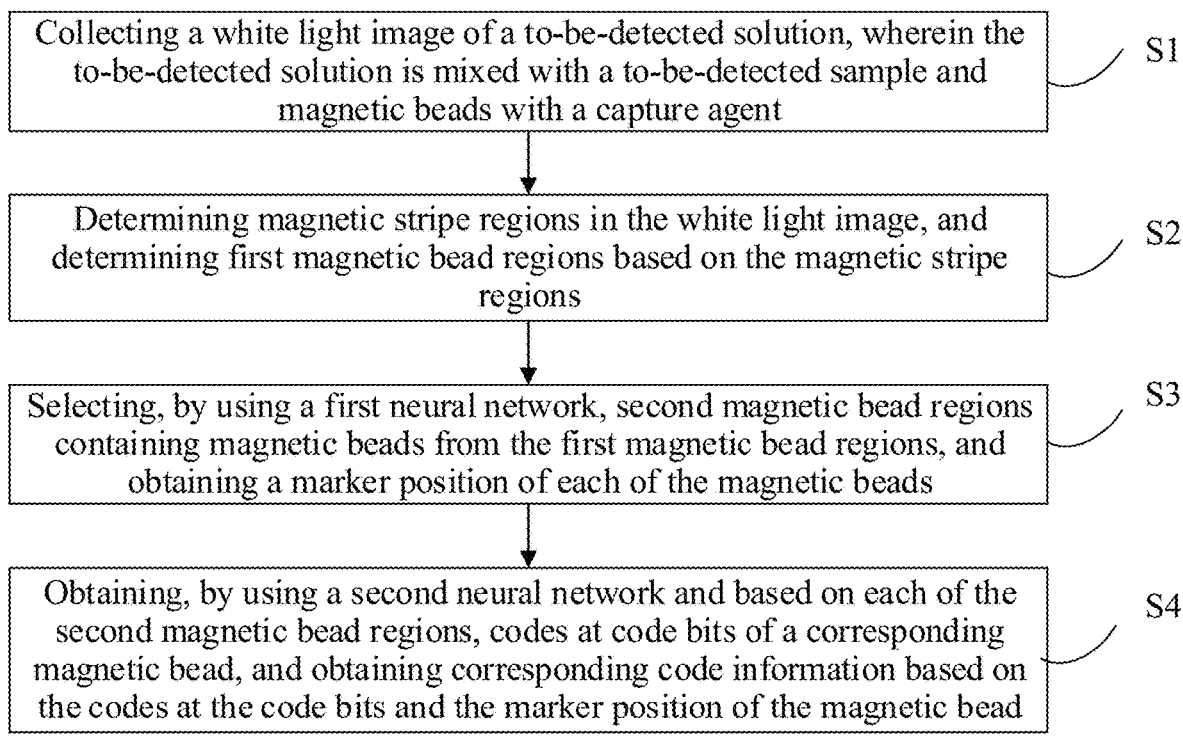
FIG. 1 is a flowchart of a magnetic bead-based detection method according to an embodiment of the present disclosure.

FIG. 1 is a flowchart of a magnetic bead-based detection method according to an embodiment of the present disclosure.

As illustrated in FIG. 1, the magnetic bead-based detection method includes the following steps:

S1, a white light image of a to-be-detected solution is collected. The to-be-detected solution is mixed with a to-be-detected sample and magnetic beads with a capture agent;

S2, magnetic stripe regions in the white light image are determined, and first magnetic bead regions are determined based on the magnetic stripe regions;

S3, second magnetic bead regions containing magnetic beads are selected from the first magnetic bead regions by using a first neural network, and a marker position of each of the magnetic beads is obtained; and S4, codes at code bits of a corresponding magnetic bead are obtained by using a second neural network and based on each of the second magnetic bead regions, and corresponding code information is obtained based on the codes at the code bits and the marker position of the magnetic bead.

In some embodiments, in order to obtain fluorescence information of the magnetic bead, a fluorescence image of the to-be-detected solution may also be collected.

Figure 2:
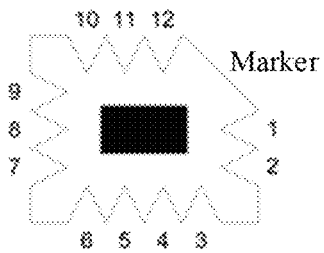
FIG. 2 is a schematic diagram of a magnetic bead according to an example of the present disclosure.
Figure 3:
FIG. 3 is a schematic diagram of code bits of a magnetic bead according to an example of the present disclosure.
Figure 4:
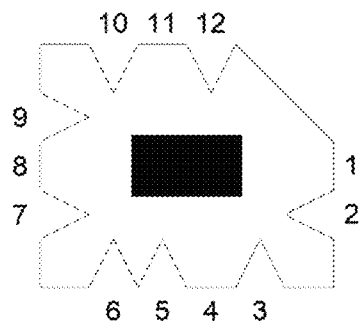
FIG. 4 is a schematic diagram of codes of a magnetic bead according to an example of the present disclosure.
Figure 4:
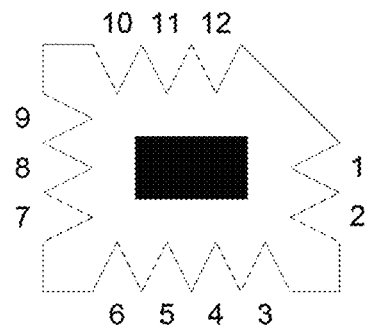

In the embodiments of the present disclosure, as illustrated in FIG. 2, appearances of the magnetic beads used in the present disclosure may be used as codes. The magnetic beads have advantages such as simple manufacture, low cost, and convenient recognition. Referring to FIG. 2, the magnetic bead includes multi-bit binary codes such as 12-bit codes. The magnetic bead has a black magnetic stripe disposed in a middle of the magnetic bead, and the magnetic stripe is recorded as a magnetic stripe. A "gap" occurs at a top-right corner, which is recorded as a marker, and is used for destroying a symmetric structure of the magnetic beads to mark a magnetic bead orientation. In a plurality of code bits, two cases occur in each code bit, such as a triangle and a plane as illustrated in FIG. 3, which corresponds to binary 0 and 1; and as illustrated in FIG. 4, determining whether the code bit is 0 or 1 by determining whether each code bit is triangular or planar.

Figure 5:
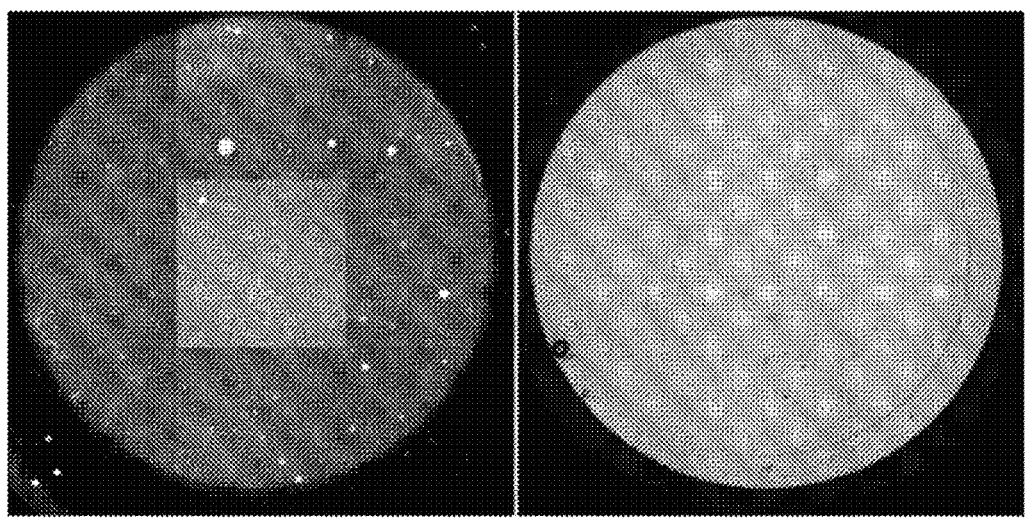
FIG. 5 is a schematic diagram of a white light image and a fluorescence image according to an example of the present disclosure.
Figure 6:
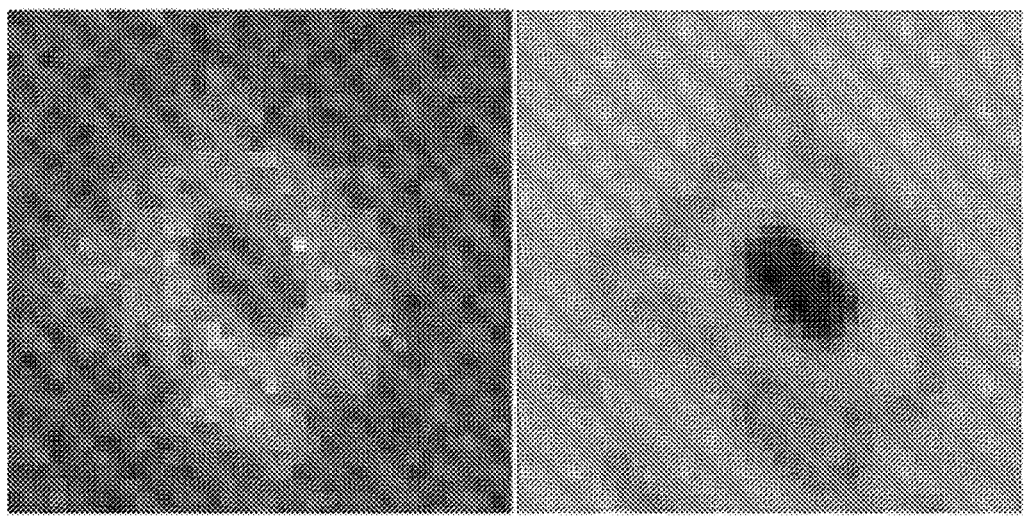
FIG. 6 is a schematic diagram of a partial region including a magnetic bead in a white light image and a fluorescence image according to an example of the present disclosure.

When immunodetection detection or molecular detection is performed, the magnetic beads with the capture agent may be mixed with the to-be-detected sample to obtain the to-be-detected solution. The to-be-detected solution may be disposed in a detection hole on a storage plate (such as a rectangular plate). There may be one or more detection holes on the storage plate. Further, the white light image and the fluorescence image may be collected through each detection hole. The white light image includes position information, region information, morphology information, and the like of the magnetic bead, and the fluorescence image includes the fluorescence information of the magnetic bead. Since a gap between capturing the white light image and the fluorescent image is very short, displacements of the magnetic beads during this gap can be considered negligible. Therefore, as illustrated in FIG. 5 and FIG. 6, it can be considered that the positions of the magnetic beads on the white light image and the fluorescent image are the same. In FIG. 5, the left side shows the fluorescence image, and the right side shows the white light image. In FIG. 6, the left side shows the fluorescence image of the magnetic beads, and the right side shows the white light image of the magnetic beads.

In an implementation, the operation of determining the magnetic stripe regions in the white light image may include: obtaining a first image through performing binarization processing on the white light image; and obtaining the magnetic stripe regions based on the first image.

In some examples, the operation of obtaining the magnetic stripe regions based on the first image may include: calculating areas and lengths of all connected regions in the first image; and determining connected regions having an area greater than or equal to a first predetermined area and smaller than or equal to a second predetermined area and a length smaller than or equal to a first predetermined length as the magnetic stripe regions.

In an implementation, the operation of determining the first magnetic bead regions based on the magnetic stripe regions may include: calculating, based on each of the magnetic stripe regions, a minimum bounding rectangle of a corresponding magnetic bead, and determining minimum bounding rectangles as the first magnetic bead regions.

Figure 7:
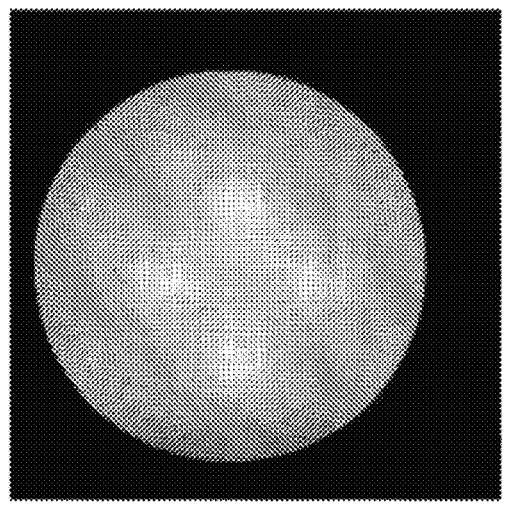
FIG. 7 is a schematic diagram of a white light image and a binarization image thereof according to an example of the present disclosure.
Figure 7:
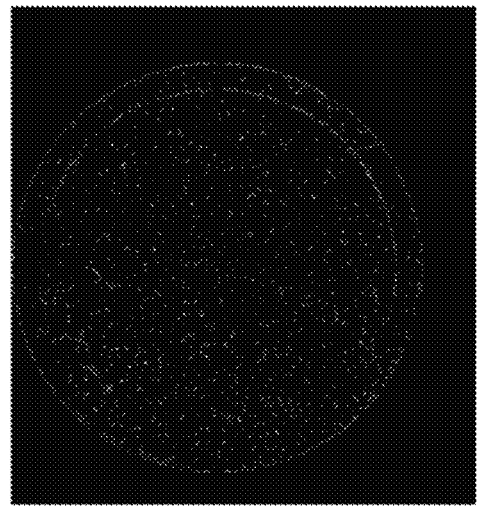
Figure 8:
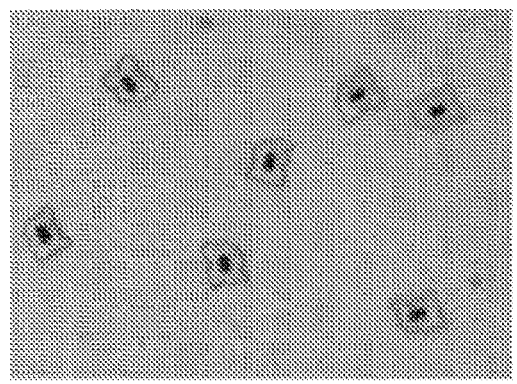
FIG. 8 is a schematic diagram of a partial white light image and a binarization image thereof according to an example of the present disclosure.
Figure 8:
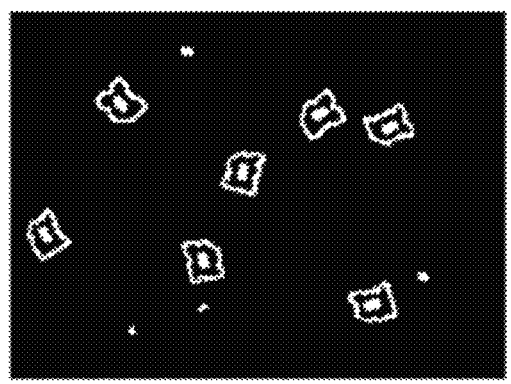

In an exemplarily embodiment of the present disclosure, the collected white light image may be binarized through a local threshold method (such as with a search window size of 9 and a threshold of 3). For example, as illustrated in FIG. 7 and FIG. 8, an intermediate image is obtained through setting a pixel value of a pixel point greater than a predetermined pixel value in the white light image as 255 and a pixel value of a pixel point smaller than or equal to the predetermined pixel value in the white light image as 0. Further, the first image is obtained through performing color inversion processing on the intermediate image, i.e., changing the pixel value of 255 to 0 and the pixel value of 0 to 255. In FIG. 7, the left side is the white light image, and the right side is a binarized first image. In FIG. 8, the left side is a partial image of the fluorescence image, and the right side is a binarized image of the partial image. For another example, the first image may be obtained by setting the pixel value of the pixel point greater than the predetermined pixel value in the white light image as 255 and the pixel value of the pixel point smaller than or equal to the predetermined pixel value in the white light image as 0.

After the first image is obtained, the connected region is determined according to the pixel value of the first image.

Figure 9:
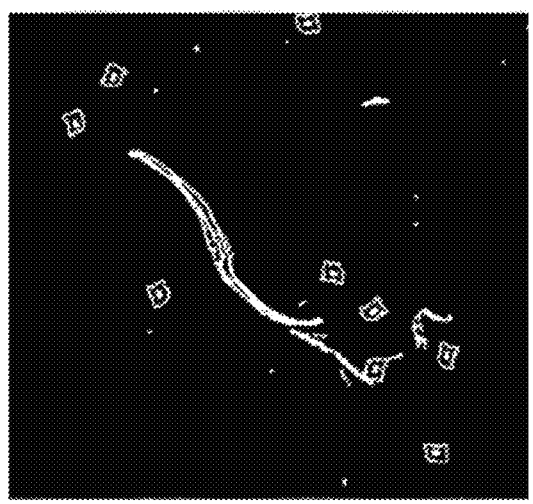
FIG. 9 is a schematic diagram of selecting a magnetic stripe region according to an example of the present disclosure.
Figure 9:
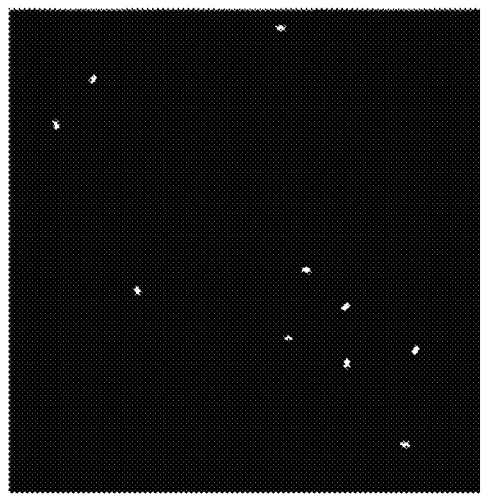

Then, a region of a black stripe in the middle of the magnetic beads, i.e., the magnetic stripe region, is preliminarily obtained through selecting based on an area, and a length and width of the connected region. When the area of the connected region is greater than a second predetermined area such as 200 or smaller than a first predetermined area such as 100, it is considered that the connected region is a non-target region. When the length and/or width of the connected region is greater than the first predetermined length such as 25, it is considered that the connected region is the non-target region. As illustrated in FIG. 9, the rest of selected connected regions (i.e., except for the non-target region) are magnetic bead black stripe regions. In FIG. 9, the left side is an image before selecting, and the right side is the selected image.

Figure 10:
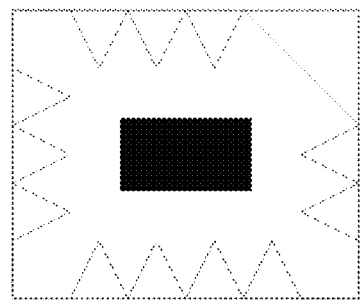
FIG. 10 is a schematic diagram of obtaining a first magnetic bead region based on a magnetic stripe region according to an example of the present disclosure.

After the middle black stripe is preliminarily selected, the black stripe in the middle of the magnetic bead is parallel to an outer contour of the magnetic bead. Moreover, the position of the black stripe in the magnetic bead is fixed. Therefore, an inclination angle of the magnetic bead can be obtained by analyzing an inclination angle of the middle black stripe. In addition, a minimum bounding rectangle of the magnetic bead can be calculated through a center position and the inclination angle of the black stripe. As illustrated in FIG. 10, the minimum bounding rectangle is the first magnetic bead region.

Figure 12:
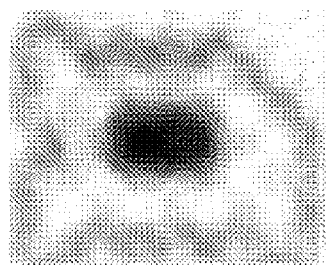
Figure 13:
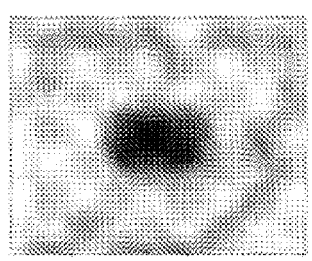
Figure 14:
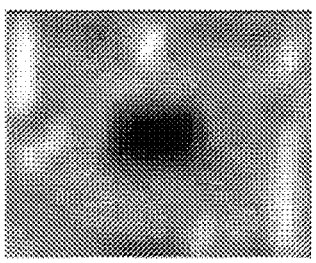
Figure 15:
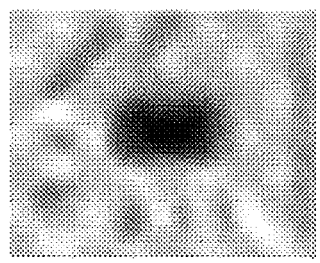
Figure 16:
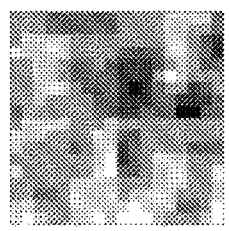
FIG. 16 to FIG. 20 are schematic diagrams of a spliced image according to some examples of the present disclosure.
Figure 17:
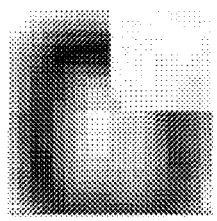
Figure 18:
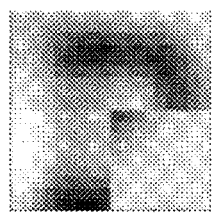
Figure 19:
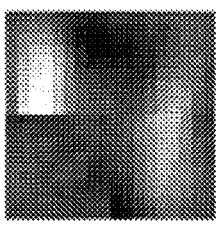
Figure 20:
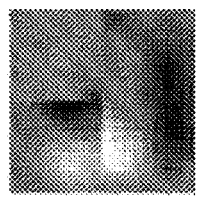

In order to facilitate subsequent code recognition, the first magnetic bead region can be cropped and aligned through rotation. It should be noted that since the middle black stripe can only obtain inclination information and position information of the magnetic bead, and cannot obtain orientation information of the magnetic bead. Moreover, some impurities may have shapes similar to the black stripe and can be recognized as magnetic beads. Therefore, the aligned image through rotation has five cases. As illustrated in FIG. 11 to FIG. 15, FIG. 11 shows the presence of impurities. FIG. 12 shows a case where the marker is at the top-right corner. FIG. 13 shows a case where the marker is at the lower-right corner. FIG. 14 shows a case where the marker is at the lower-left corner. FIG. 15 shows a case where the marker is at the top-left corner.

In an implementation, the operation of selecting, by using the first neural network, the second magnetic bead regions containing magnetic beads from the first magnetic bead regions, and obtaining the marker position of the each of the magnetic beads may include: extracting n×n regions on each of four corners of each of the first magnetic bead regions, and forming a 2n×2n spliced image through sequentially splicing the four n×n regions, where n is a positive integer; inputting a first pixel matrix corresponding to pixels in the spliced image into the first neural network, and outputting a category of the spliced image, in which the category includes impurities, a top-left corner marker, a top-right corner marker, a lower-left corner marker, and a lower-right corner marker; and determining, based on the category, whether the first magnetic bead region includes a magnetic bead, taking the first magnetic bead region as a second magnetic bead region in response to determining that the first magnetic bead region includes the magnetic bead, and obtaining the marker position of the magnetic bead.

Here, the first neural network may include a first convolution layer, a first pooling layer, a second convolution layer, a second pooling layer, a first full connection layer, a second full connection layer, and a third full connection layer that are sequentially connected to each other.

Figure 11:
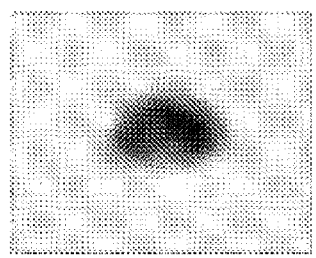
FIG. 11 to FIG. 15 are schematic diagrams of a first magnetic bead region according to some examples of the present disclosure.

In the embodiments of the present disclosure, since images corresponding to the aligned first magnetic bead region through rotation have five cases, for the convenience of subsequent code reading, it is necessary to selecting the impurities illustrated in FIG. 11 and unify the magnetic bead rotation images. For example, the sizes of the images are unified through a scaling method. In order to distinguish the above five types of cases and to avoid the addition of interference from different codes, the first magnetic bead region needs to be selected and subjected to posture correction.

In an exemplarily embodiment of the present disclosure, n×n regions, such as 9×9 regions, on each of four corners of each of the magnetic bead rotation images may be extracted. Moreover, a 2n×2n image such as 18×18 image is formed through sequentially splicing the n×n regions such as 9×9 regions and is taken as a classification standard. As illustrated in FIG. 16 to FIG. 20, the classification standards are spliced images classified as impurities, a having a top-right corner marker a lower-right corner marker, a lower-left corner marker, and a top-left corner marker sequentially. Therefore, the orientation of the magnetic beads is determined by using the spliced images at four corners, which can avoid interference from different codes on algorithm recognition. As a result, the workload of preparing training samples, complexity of the algorithm, and an operation time are greatly reduced.

In order to distinguish the category of each spliced image, each pixel of the spliced image may be normalized to a value between 0 and 1 by using the following equation:

$$X\_nor = \frac{X - X\_min}{X\_max - X\_min}$$

where X_nor represents a normalized pixel value of a pixel value of X, X_min represents a minimum pixel value in the spliced image, X_max represents a maximum pixel value in the spliced image.

Figure 21:
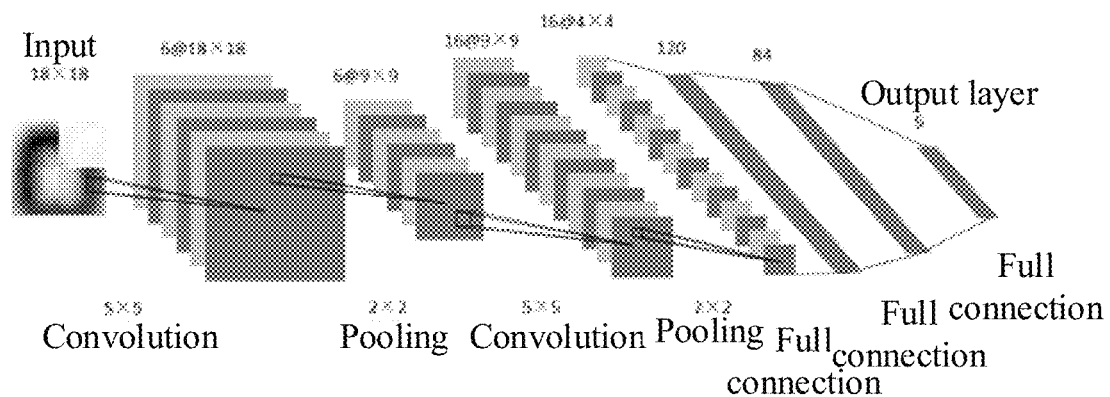
FIG. 21 is a schematic diagram of a first neural network according to an example of the present disclosure.

The normalized pixel value matrix is determined as an input of the first neural network to determine the categories of the spliced image. The first neural network may use a convolutional neural network, which has a structure as illustrated in FIG. 21 and the advantages of high robustness and fast operation speed. After the categories of the spliced images are obtained, the first magnetic bead regions, which are determined as the impurities, are removed, and the rest of regions are the second magnetic bead regions containing the magnetic beads. Moreover, as illustrated in FIG. 12 to FIG. 15, the second magnetic bead regions are rotated to a specified position to obtain a correctly aligned image of the magnetic bead through rotation.

In some embodiments, the first neural network may also be a deep learning network.

In an implementation, the operation of obtaining, by using the second neural network and based on each of the second magnetic bead regions, the codes at the code bits of the corresponding magnetic bead includes: obtain a plurality of code images through extracting m×m regions of each of the code bits of the corresponding magnetic bead in the second magnetic bead region, where m is a positive integer; and inputting each of second pixel matrixes corresponding to pixels in the plurality of code images into the second neural network, and outputting codes corresponding to the plurality of code images.

Here, the second neural network may include a third convolution layer, a fourth convolution layer, a fourth full connection layer, a fifth full connection layer, and a sixth full connection layer that are sequentially connected to each other.

In an exemplarily embodiment of the present disclosure, after the correctly aligned image of the magnetic bead through rotation is obtained, the position of each code bit on the image is fixed. Therefore, it is only necessary to extract the image at the corresponding position and determine whether each small image is 0 or 1, so as to obtain the code of each magnetic bead.

Figure 22:
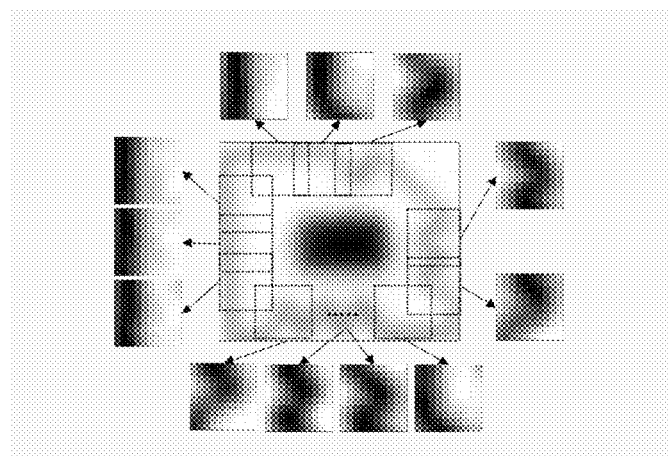
FIG. 22 is a schematic diagram of extracting a code bit according to an example of the present disclosure.
Figure 23:
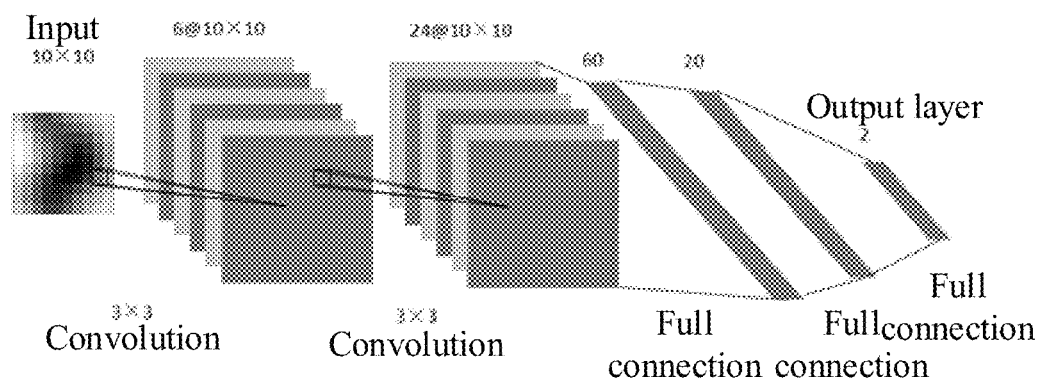
FIG. 23 is a schematic diagram of a second neural network according to an example of the present disclosure.

Each magnetic bead may extract 12 small images with codes. As illustrated in FIG. 22, each code small image has a size of 10×10. These small images can be normalized to a value between 0 and 1 by using formula 1, and then used as an input of the second neural network to determine whether each small image is 0 or 1, thereby obtaining the codes of the magnetic beads. The second neural network may adopt a convolutional neural network, which has a network structure as illustrated in FIG. 23 and has the advantages of high robustness and high operation speed.

In another implementation, after the categories of the spliced image are obtained, rotation or rolling-over treatment may be performed, allowing the markers of the magnetic beads to be in a predetermined position. For example, all are on the top-right corner. Further, the marker of each magnetic bead is obtained. Moreover, the plurality of code images is obtained through extracting the m×m regions of each of the code bits of the magnetic bead in the second magnetic bead region. In other embodiments of the present disclosure, different markers correspond to different extraction manners, to extract the m×m regions of each of the code bits of the magnetic bead in the second magnetic bead region to obtain the plurality of code images.

In yet another implementation, after the categories of the spliced image are obtained, rotation or rolling-over treatment cannot be performed, but the marker of each magnetic bead is directly obtained. Further, the plurality of code images is obtained through extracting the m×m regions of each of the code bits of the magnetic bead in the second magnetic bead region. In other embodiments of the present disclosure, different markers correspond to different extraction manners, to extract the m×m regions of each of the code bits of the magnetic bead in the second magnetic bead region to obtain the plurality of code images.

In some embodiments of the present disclosure, the detection method may further include: obtaining fluorescence information of the corresponding magnetic bead based on the fluorescence image and a magnetic stripe region in the second magnetic bead region.

In an implementation, the operation of obtaining the fluorescence information of the corresponding magnetic bead based on the fluorescence image and the magnetic stripe region in the second magnetic bead region may include: determining a rectangular region around the magnetic stripe region within a predetermined range as a first fluorescence extraction region of the corresponding magnetic bead; determining a second fluorescence extraction region in the fluorescence image based on the first fluorescence extraction region; obtaining a first median of pixel values in the second fluorescence extraction region; and determining the first median as the fluorescence information of the corresponding magnetic bead.

Figure 24:
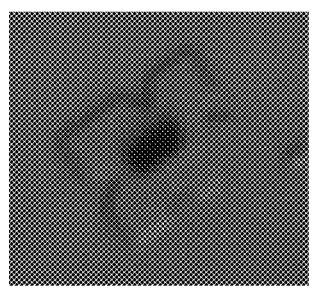
FIG. 24 is a schematic diagram of edge blur of a magnetic bead according to an example of the present disclosure.
Figure 25:
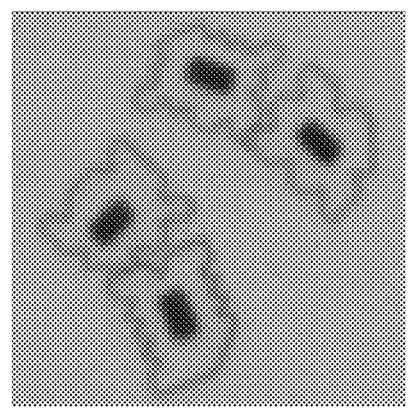
FIG. 25 is a schematic diagram of overlapping occurring in magnetic beads according to an example of the present disclosure.
Figure 26:
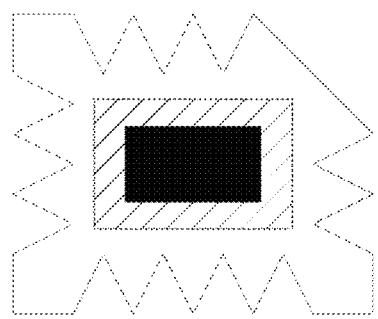
FIG. 26 is a schematic diagram of a fluorescence reading region according to an example of the present disclosure.

In an exemplarily embodiment of the present disclosure, considering that the magnetic beads are made of transparent materials and their edges in the white light image are generated by light refraction, as illustrated in FIG. 24, the edges of the magnetic beads at some positions may be very blurry and even invisible to the naked eye. As illustrated in FIG. 25, an overlap may occur between the magnetic beads, it is difficult to obtain a specific contour of each magnetic bead. In addition, the black stripe is opaque, causing abnormally low fluorescence values in that region, which does not reflect a true case of the sample. Therefore, in the present disclosure, a fixed region around the black stripe is used as the fluorescence extraction region of each magnetic bead, i.e., a pixel rectangular region with a size of 17×11, with a center of the black stripe as the center and an inclination angle of the black stripe as the inclination angle. By excluding the black stripe region from this rectangular region, the second fluorescence extraction region for extracting the fluorescence of the magnetic beads can be obtained. As illustrated in FIG. 26, a diagonal stripe in the image represents the second fluorescence extraction region of the magnetic bead. A median of the pixel value of the region is obtained to be determined as the fluorescence information of the magnetic bead.

In another exemplarily embodiment of the present disclosure, the corresponding fluorescent magnetic stripe region in the fluorescence image may also be determined according to the magnetic stripe region in the second magnetic bead region. Further, a rectangular region around the fluorescent magnetic stripe region within the predetermined range is directly used as the second fluorescence extraction region of the corresponding magnetic bead.

Due to uneven laser illumination and an uneven liquid surface, fluorescent reaction intensities of the magnetic beads at different positions are different. Therefore, the influence of this factor needs to be removed. To this end, in some embodiments, the magnetic bead-based detection method may further include: obtaining a background value of the corresponding magnetic bead based on the first image; and correcting the fluorescence information by using the background value, i.e., determining a level of illumination at the position by the background value, and then subtracting the corresponding background fluorescence value from the fluorescence value of the magnetic bead itself (the above obtained fluorescence information).

In an implementation, the operation of obtaining the background value of the corresponding magnetic bead based on the first image includes: obtaining a second image through filling a hole having a first pixel value (such as 255) in the first image; determining a region, in the white light image or the fluorescence image, corresponding to a region where a second pixel value (such as 0) in the second image is located, and obtaining a second median of brightness values of the region; and determining the second median as the background value.

Figure 27:
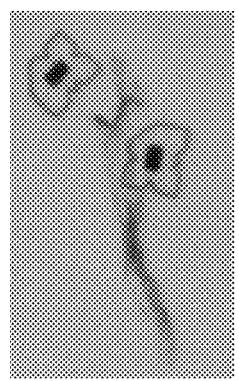
FIG. 27 is a schematic diagram of filling a hole according to an example of the present disclosure.
Figure 27:
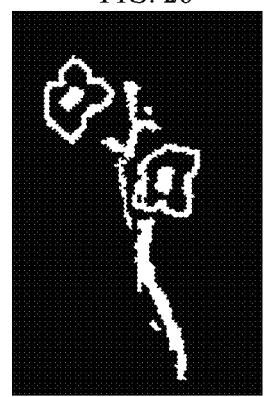
Figure 27:
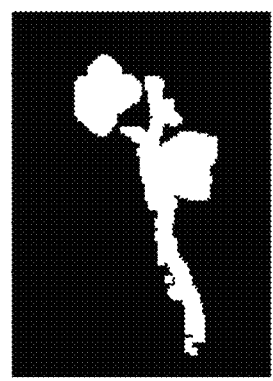

In an exemplarily embodiment of the present disclosure, a background region of the magnetic bead is selected. Considering the problems of reading loss and impurities of the magnetic beads, regions where magnetic beads are not recognized should not be considered as the background region. To this end, the present disclosure fills a hole in the first image. As illustrated in FIG. 27, the black region (i.e., a region with the pixel value of 0) in the image is the background region of the magnetic bead, and a median brightness of the white light image or the fluorescent image corresponding to the region is used as the background value of the magnetic bead. In FIG. 27, the left image is the white light image, the intermediate image is a binarization image corresponding to the left image, and the right image is an image after the hole is filled.

After the background value is obtained, the background value is subtracted from the fluorescence value of the magnetic bead, such that the corrected fluorescence value of the magnetic bead can be obtained. Therefore, the influence of some impurities and unidentified magnetic beads on the background value can be avoided.

After the code information and the fluorescence information are obtained, sample information of the to-be-detected sample may be obtained according to the code information and the fluorescence information.

In an exemplarily embodiment of the present disclosure, for multiple detection, the code information in the sample information of the same sample is the same. Therefore, the sample information can be classified according to all code information obtained in one detection. Further, the sample information of all the samples is obtained. In this way, quantitative detection on each to-be-detected sample is facilitated.

With the magnetic bead-based detection method according to the embodiments of the present disclosure, the orientation of the magnetic beads is determined by adopting the spliced images on the four corners of the image. In this way, the interference from different codes on algorithm recognition can be avoided. Therefore, the workload of preparing the training samples, the complexity, and the operation time of the algorithm are greatly reduced. The orientation determination and code recognition of the magnetic beads are realized by using the convolutional neural network, which has the advantages of high robustness and fast operation speed. The fluorescence of the fixed region is read as the magnetic bead fluorescence, which has the advantages of being high in speed, being insusceptible to unclear boundaries, high in accuracy, consistent in different code extraction regions (areas of the magnetic beads in different codes may vary), and the like.

Based on the magnetic bead-based detection method described above, the present disclosure provides a computer-readable storage medium.

In the embodiments of the present disclosure, the computer-readable storage medium stores a computer program. The computer program, when executed by a processor, implements the magnetic bead-based detection method as described above.

Based on the above magnetic bead-based detection method, the present disclosure provides a detection device.

Figure 28:
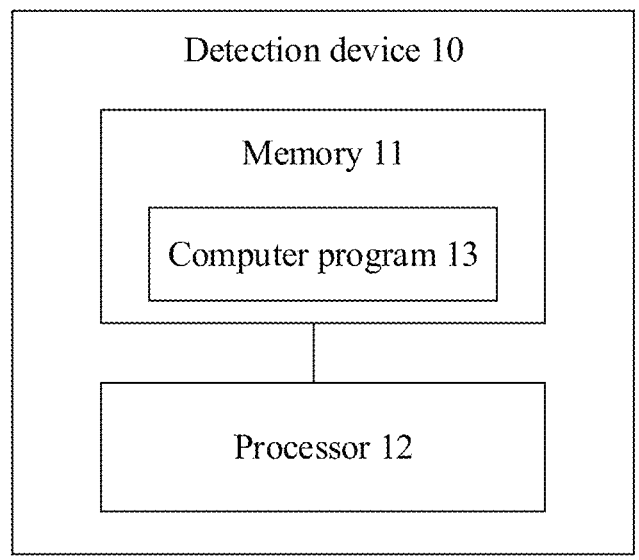
FIG. 28 is a structural block diagram of a detection device according to an embodiment of the present disclosure.

In the embodiments of the present disclosure, as illustrated in FIG. 28, a detection device 10 includes a memory 11, a processor 12, and a computer program 13 stored on the memory 11. The computer program 13, when executed by the processor 12, implements the magnetic bead-based detection method as described above.

Here, the detection device 10 may be an upper computer. The upper computer may be connected to an image collection apparatus that captures the white light image and the fluorescence image. In this way, the white light image and the fluorescence image are obtained from the image collection apparatus.

In the description of this specification, descriptions with reference to the terms "an embodiment," "some embodiments," "schematic embodiments," "examples," "specific examples," or "some examples," etc. mean that specific features, structure, materials or characteristics described in conjunction with the embodiment or example are included in at least one embodiment or example of the present disclosure. In this specification, the schematic representations of the above terms do not necessarily refer to the same embodiment or example.

Although the embodiments of the present disclosure are illustrated and described above, it can be understood by those of ordinary skill in the art that various changes, modifications, substitutions and alterations may be made to these embodiments without departing from the principles and spirit of the present disclosure. The scope of the present disclosure is defined by the claims and their equivalents.

What is claimed is:

1. A magnetic bead-based detection method, comprising:
collecting a white light image of a to-be-detected solution, wherein a to-be-detected sample and magnetic beads with a capture agent are mixed in the to-be-detected solution;
determining magnetic stripe regions in the white light image;
determining first magnetic bead regions based on the magnetic stripe regions;
selecting, by using a first neural network, second magnetic bead regions containing magnetic beads from the first magnetic bead regions, and obtaining a marker position of each of the magnetic beads;
obtaining, by using a second neural network and based on each of the second magnetic bead regions, codes at code bits of a corresponding magnetic bead; and
obtaining corresponding code information based on the codes at the code bits of the magnetic bead and the marker position of the magnetic bead.

2. The method according to claim 1, wherein said determining the magnetic stripe regions in the white light image comprises:
obtaining a first image through performing binarization processing on the white light image; and
obtaining the magnetic stripe regions based on the first image.

3. The method according to claim 2, wherein said obtaining the first image through performing binarization processing on the white light image comprises:
obtaining an intermediate image through setting a pixel value of a pixel point greater than a predetermined pixel value in the white light image as 255 and a pixel value of a pixel point smaller than or equal to the predetermined pixel value in the white light image as 0; and
obtaining the first image through performing color inversion processing on the intermediate image.

4. The method according to claim 2, wherein said obtaining the magnetic stripe regions based on the first image comprises:
calculating areas and lengths of all connected regions in the first image; and
determining connected regions having an area greater than or equal to a first predetermined area and smaller than or equal to a second predetermined area and a length smaller than or equal to a first predetermined length as the magnetic stripe regions.

5. The method according to claim 1, wherein said determining the first magnetic bead regions based on the magnetic stripe regions comprises:
calculating, based on each of the magnetic stripe regions, a minimum bounding rectangle of a corresponding magnetic bead, and determining minimum bounding rectangles as the first magnetic bead regions.

6. The method according to claim 1, wherein said selecting, by using the first neural network, the second magnetic bead regions containing magnetic beads from the first magnetic bead regions, and obtaining the marker position of each of the magnetic beads comprises:
extracting n×n regions on each of four corners of each of the first magnetic bead regions, and forming a 2n×2n spliced image through sequentially splicing the four n×n regions, where n is a positive integer;
inputting a first pixel matrix corresponding to pixels in the spliced image into the first neural network, and outputting a category of the spliced image, wherein the category comprises impurities, a top-left corner marker, a top-right corner marker, a lower-left corner marker, and a lower-right corner marker; and
determining, based on the category, whether the first magnetic bead region comprises a magnetic bead, determining the first magnetic bead region as a second magnetic bead region in response to determining that the first magnetic bead region comprises the magnetic bead, and obtaining the marker position of the magnetic bead.

7. The method according to claim 6, wherein the first neural network comprises a first convolution layer, a first pooling layer, a second convolution layer, a second pooling layer, a first full connection layer, a second full connection layer, and a third full connection layer that are sequentially connected to each other.

8. The method according to claim 1, wherein said obtaining, by using the second neural network and based on each of the second magnetic bead regions, the codes at the code bits of the corresponding magnetic bead comprises:
obtaining a plurality of code images through extracting m×m regions of each of the code bits of the corresponding magnetic bead in the second magnetic bead region, where m is a positive integer; and
inputting each of second pixel matrixes corresponding to pixels in the plurality of code images into the second neural network, and outputting codes corresponding to the plurality of code images.

9. The method according to claim 8, wherein the second neural network comprises a third convolution layer, a fourth convolution layer, a fourth full connection layer, a fifth full connection layer, and a sixth full connection layer that are sequentially connected to each other.

10. The method according to claim 1, further comprising:
collecting a fluorescence image of the to-be-detected solution; and
obtaining, based on the fluorescence image and a magnetic stripe region in the second magnetic bead region, fluorescence information of a corresponding magnetic bead.

11. The method according to claim 10, wherein said obtaining, based on the fluorescence image and the magnetic stripe region in the second magnetic bead region, the fluorescence information of the corresponding magnetic bead comprises:
determining a rectangular region around the magnetic stripe region within a predetermined range as a first fluorescence extraction region of the corresponding magnetic bead;
determining a second fluorescence extraction region in the fluorescence image based on the first fluorescence extraction region;
obtaining a first median of pixel values in the second fluorescence extraction region; and
determining the first median as the fluorescence information of the corresponding magnetic bead.

12. The method according to claim 11, further comprising:
obtaining a background value of the corresponding magnetic bead based on the first image; and
correcting the fluorescence information by using the background value.

13. The method according to claim 12, wherein said obtaining the background value of the corresponding magnetic bead based on the first image comprises:
obtaining a second image through filling a hole having a first pixel value in the first image;
determining a region, in the white light image or the fluorescence image, corresponding to a region where a second pixel value in the second image is located, and obtaining a second median of brightness values of the region; and
determining the second median as the background value.

14. A computer-readable storage medium, storing a computer program, wherein the computer program, when executed by a processor, causes the processor to:
collect a white light image of a to-be-detected solution, wherein a to-be-detected sample and magnetic beads with a capture agent are mixed in the to-be-detected solution;
determine magnetic stripe regions in the white light image;
determine first magnetic bead regions based on the magnetic stripe regions;
select, by using a first neural network, second magnetic bead regions containing magnetic beads from the first magnetic bead regions, and obtain a marker position of each of the magnetic beads;
obtain, by using a second neural network and based on each of the second magnetic bead regions, codes at code bits of a corresponding magnetic bead; and
obtain corresponding code information based on the codes at the code bits of the magnetic bead and the marker position of the magnetic bead.

15. A detection device, comprising:
a memory;
a processor; and
a computer program stored on the memory, wherein the computer program, when executed by the processor, causes the processor to:
collect a white light image of a to-be-detected solution, wherein a to-be-detected sample and magnetic beads with a capture agent are mixed in the to-be-detected solution;
determine magnetic stripe regions in the white light image;
determine first magnetic bead regions based on the magnetic stripe regions;
select, by using a first neural network, second magnetic bead regions containing magnetic beads from the first magnetic bead regions, and obtain a marker position of each of the magnetic beads;
obtain, by using a second neural network and based on each of the second magnetic bead regions, codes at code bits of a corresponding magnetic bead; and
obtain corresponding code information based on the codes at the code bits of the magnetic bead and the marker position of the magnetic bead.

16. The detection device according to claim 15, wherein said determining the magnetic stripe regions in the white light image comprises:
obtaining a first image through performing binarization processing on the white light image; and
obtaining the magnetic stripe regions based on the first image.

17. The detection device according to claim 15, wherein said selecting, by using the first neural network, the second magnetic bead regions containing magnetic beads from the first magnetic bead regions, and obtaining the marker position of each of the magnetic beads comprises:

extracting n×n regions on each of four corners of each of the first magnetic bead regions, and forming a 2n×2n spliced image through sequentially splicing the four n×n regions, where n is a positive integer;

inputting a first pixel matrix corresponding to pixels in the spliced image into the first neural network, and outputting a category of the spliced image, wherein the category comprises impurities, a top-left corner marker, a top-right corner marker, a lower-left corner marker, and a lower-right corner marker; and determining, based on the category, whether the first magnetic bead region comprises a magnetic bead, determining the first magnetic bead region as a second magnetic bead region in response to determining that the first magnetic bead region comprises the magnetic bead, and obtaining the marker position of the magnetic bead.

18. The detection device according to claim 15, wherein said obtaining, by using the second neural network and based on each of the second magnetic bead regions, the codes at the code bits of the corresponding magnetic bead comprises:

obtaining a plurality of code images through extracting m×m regions of each of the code bits of the corresponding magnetic bead in the second magnetic bead region, where m is a positive integer; and inputting each of second pixel matrixes corresponding to pixels in the plurality of code images into the second neural network, and outputting codes corresponding to the plurality of code images.

19. The detection device according to claim 15, wherein the computer program, when executed by the processor, further causes the processor to:

collect a fluorescence image of the to-be-detected solution; and obtain, based on the fluorescence image and a magnetic stripe region in the second magnetic bead region, fluorescence information of a corresponding magnetic bead.

20. The detection device according to claim 19, wherein said obtaining, based on the fluorescence image and a magnetic stripe region in the second magnetic bead region, fluorescence information of a corresponding magnetic bead comprises:

determining a rectangular region around the magnetic stripe region within a predetermined range as a first fluorescence extraction region of the corresponding magnetic bead;

determining a second fluorescence extraction region in the fluorescence image based on the first fluorescence extraction region;

obtaining a first median of pixel values in the second fluorescence extraction region; and determining the first median as the fluorescence information of the corresponding magnetic bead.

* * * * *